United States Patent [19]

Cimiluca

[11] 4,372,942
[45] Feb. 8, 1983

[54] CANDY BASE AND LIQUID CENTER HARD CANDY MADE THEREFROM

[75] Inventor: Paul A. Cimiluca, Succasunna, N.J.

[73] Assignee: Beecham Inc., Clifton, N.J.

[21] Appl. No.: 292,482

[22] Filed: Aug. 13, 1981

[51] Int. Cl.³ .......................... A23G 9/00; A61K 27/00
[52] U.S. Cl. ........................................ 424/16; 426/103;
426/660; 426/658; 424/14; 424/361; 424/193;
424/310; 424/346
[58] Field of Search .............. 426/660, 103, 512, 514,
426/515, 658, 35; 424/361, 14, 16, 78, 44, 49,
154, 176, 310, 346

[56] References Cited

U.S. PATENT DOCUMENTS

| | | | |
|---|---|---|---|
| 2,311,235 | 2/1943 | Kuderman | 426/548 |
| 3,271,256 | 9/1966 | Frey | 426/660 |
| 3,295,992 | 1/1967 | Frey | 426/660 |
| 3,438,787 | 4/1969 | Du Ross | 426/660 |
| 3,439,089 | 4/1969 | Cherkas et al. | 424/78 |
| 3,496,886 | 2/1970 | Fohr | 426/660 |
| 3,556,811 | 1/1971 | Smith | 426/660 |
| 4,127,645 | 11/1978 | Witzel et al. | 424/44 |
| 4,229,482 | 10/1980 | Kreske | 426/660 |
| 4,229,484 | 10/1980 | Steels | 426/660 |
| 4,260,596 | 4/1981 | Mackles | 424/16 |
| 4,271,142 | 6/1981 | Puglia et al. | 424/14 |

FOREIGN PATENT DOCUMENTS 1481738  8/1977  United Kingdom ................ 426/660

OTHER PUBLICATIONS

"Sorbitol and Mannitol in Confections", The Manufacturing Confectioner, Nov., 1979, pp. 23–28.

*Primary Examiner*—Jeanette M. Hunter
*Attorney, Agent, or Firm*—Jacobs & Jacobs

[57] ABSTRACT

A candy base which comprises, before cooking, from about 35 to about 60%, by weight, sucrose, from about 55 to about 35%, by weight, corn syrup and from about 1 to about 10% by weight of a fluidizing agent selected from the group consisting of mannitol and a mixture of mannitol and sorbitol having a weight ratio of mannitol to sorbitol of at least about 1:1.

16 Claims, No Drawings

CANDY BASE AND LIQUID CENTER HARD CANDY MADE THEREFROM

The present invention relates to a candy base suitable for preparing liquid-center hard candy, and to hard candy prepared from the candy base.

Hard candy has been prepared with a liquid center, e.g., a cough drop comprising a medicated, liquid "cough syrup" in a hard candy shell, by means of a depositing process, wherein the liquid center is enveloped by candy base and both the center and the candy shell are co-deposited into a mold. In the depositing process, both the center and shell material can be metered with accuracy and precision.

There are problems associated with the use of the depositing process. The primary difficulty is that the candy base must be extremely fluid at the depositing temperature in order to accept a liquid center. The degree of fluidity required of the candy base is, to a certain extent, dependent upon the viscosity of the liquid center. If the center material is quite viscous at depositing temperature, the candy base may be somewhat less fluid. However, in order to be perceived as "liquid", the center's viscosity must be limited. Until now, it has not been possible to prepare a candy base with a sucrose-glucose weight ratio in the range 60/40 to 50/50 which when cooked to a low moisture content (2–3%) remained fluid enough to accept a "liquid center". If the candy base is cooked to a lower temperature, more residual moisture is present in the candy. Moisture levels of 4–5% cause the candy base to be sufficiently fluid to accept a liquid center. However, high moisture levels are not acceptable because of the shelf-life requirements of pharmaceutical products. At 4–5% moisture, candy base readily crystallizes and becomes opaque.

Historically, sugar doctors, such as invert sugar, have been used to inhibit the crystallization of sucrose. Invert sugar may be added externally or generated in situ by the addition of an acid which catalyzes the hydrolysis of sucrose. Invert sugar may also be formed thermally during cooking. Because invert sugar inhibits sucrose crystallization, it also causes the candy base to be more fluid. However, invert sugar is hygroscopic. The level of invert sugar must be carefully controlled or the candy will pick up moisture and become tacky. In order to produce a sufficiently fluid candy base for liquid center depositing, too much invert sugar would have to be added or generated in processing. Once again the candy would not be sufficiently stable.

The present invention now provides a candy base suitable for use in a depositing process based upon the use of mannitol or a mixture of mannitol and sorbitol to fluidize the candy base during processing and to stabilize the candy base against crystallization during storage. In particular, the present invention provides a candy base, which comprises (before cooking) sucrose in an amount of from about 35 to about 60%, preferably about 40 to about 55%, by weight, corn syrup in an amount of from about 55 to about 35%, preferably about 55 to about 40%, by weight, from about 1 to about 10%, preferably about 2 to about 8%, by weight, of mannitol or a mixture of mannitol and sorbitol having a weight ratio of mannitol to sorbitol of at least about 1:1, preferably from 1:1 to about 9:1, all based on the total weight of the candy base. Most preferably, the amount of sucrose is about 48 to about 53%, the amount of glucose is about 50 to about 40%, and the mannitol or mannitol/sorbitol mixture is about 2 to about 3%.

The mannitol or mixture of mannitol and sorbitol, acts as a "sugar doctor" in the sense that it inhibits crystallization of the candy base during storage. In addition, these agents also fluidize the candy base so that the candy base can be used in a depositing process to accept a liquid center. It has also been found that the mannitol (with or without sorbitol) provides the following additional advantages:

(a) It gives rise to a clear, transparent candy;
(b) It reduces the setting temperature of the candy base so that relatively high quantities of solids can be incorporated into the candy base over a greater time period than would otherwise be possible;
(c) It reduces the setting temperature of the candy base so that volatile medicaments or flavors can be added at lower temperatures with lower losses from evaporation; and
(d) It reduces the hygroscopicity of the finished piece making it less susceptible to moisture pick-up and subsequent tackiness.

Sorbitol and mannitol are known as non-sugar sweeteners. Mannitol has been proposed for use as a doctor for sorbitol hard candy, and various polyhydroxy compounds, including sorbitol, have been proposed for use in combination with water and non-hygroscopic polyethylene glycol to assist in incorporating chloroform into hard candy. See "The Manufacturing Confectioner for November, 1979", pages 23-18, and U.S. Pat. No. 3,721,256. So far as I am aware, however, there has not been any disclosure of the use of mannitol or a mixture of mannitol and sorbitol as a fluidizing and anti-crystallization agent in sucrose/corn syrup hard candy.

The candy base of the present invention is prepared by cooking sucrose and corn syrup to a moisture content of from about 1.5 to about 3% by weight. A cooking temperature within the range of from about 150° to about 160° C., preferably from about 155° C. to about 160° C., can be used. The cooking may be at atmospheric pressure or under vacuum, as is known. Conventional cookers used to cook and remove water from candy base may be used.

The mannitol or mixture of mannitol and sorbitol, is conveniently added to the candy base by dissolving the same in water along with the sucrose at elevated temperature, admixing the solution with corn syrup and sending the final mix to the cooking step during which water is removed.

Useful results are obtained within the range of from about 1 to about 10% mannitol (or mannitol/sorbitol mixture), but mixtures of sucrose and glucose with a higher sucrose content tend to require a larger amount of additive. Thus, the performance of a candy base may be improved by increasing the amount of additive at a given sucrose to corn syrup ratio or by decreasing the sucrose to corn syrup ratio or both. Candy base prepared at lower sucrose to corn syrup ratios, such as 50:50, were harder than those prepared at higher sucrose to corn syrup ratios, e.g. 55:45.

I have also found that from about 5 to about 15% lactose, by weight, can be used in place of the 1 to 10% mannitol or mannitol/sorbitol mixture, but I prefer to use mannitol or mannitol/sorbitol.

All of the ingredients for the candy base of the present invention are commercially available. Preferably, regular conversion corn syrup [43° Be; 42 dextrose equivalent ("DE)] or high maltose corn syrup is employed, but high conversion (56DE) or low conversion (36DE) corn syrup can also be used. Low conversion corn syrup is not suitable for use in a depositing process because it is too viscous, but it can be used to make non-filled candy. Both regular and high conversion corn syrup can be used in the depositing process, but high conversion syrup gives a candy product suitable only as a confection. Regular conversion corn syrup and high maltose corn syrup provide a stable, non-hygroscopic, liquid-center product of a quality suitable for pharmaceutical applications, such as lozenges, cough drops and the like.

The choice of liquid center for use with the candy base of the invention is dictated by known parameters. The specific gravity of the center material should match that of the candy base (about 1.5) so that the center and candy base are in gravitational equilibrium during the depositing process. In addition, the viscosity of the center should also match that of the candy base to prevent the center material from becoming located at the side of the candy with either no shell or an unsatisfactorily thin shell on the outside. Suitable center materials will generally be a mixture of sucrose, glycerin and corn syrup cooked to a relatively low moisture content of about 5 to about 10%. Where a placebo or a confection is desired, no active materials will be included in the center, but if a pharmaceutical product is desired, e.g., a medicated lozenge or cough drop, a pharmaceutical material will be included, such as dextromethorphan hydrobromide, phenol, benzocaine, hexylresorcinol and the like.

Typical liquid centers for use in the invention will have the "cooked" composition set forth below:

| Type "A" Center | | |
|---|---|---|
| | Broad Range (%) | Preferred (%) |
| Sucrose | 10–30 | 20 |
| Invert Sugar | 1–10 | 5 |
| Corn Syrup Solids | 30–70 | 40 |
| Glycerin | 20–40 | 30 |
| Water | 5–10 | 5 |

| Type "B" Center | | |
|---|---|---|
| | Broad Range (%) | Preferred (%) |
| Sorbitol | 10–60 | 30 |
| Glycerin | 10–60 | 30 |
| Corn Syrup Solids | 30–70 | 35 |
| Water | 5–10 | 5 |

In both cases, the liquid centers are prepared by cooking the ingredients, minus glycerin, to about 145°–150° C. to provide a moisture content of about 5 to about 10%, preferably about 5%. After cooling to about 100°–110° C., the glycerin is added with stirring. When sorbitol is employed, it is preferred that the sorbitol be added in aqueous solution, such as a 70% aqueous sorbitol solution.

Liquid centers of Type "A" and "B" have a specific gravity of about 1.40, which is sufficiently close to the specific gravity of about 1.50 for the candy base. They also have a viscosity of about 5,000 to about 40,000 cps. (50° C.), preferably about 10,000 to about 20,000 cps, to make them suitable for use in a "depositor" described below.

The candy base of the invention is particularly suited for use in a high-boil, sweets depositor (hereinafter referred to as a "depositor") used in the industry to prepare liquid-center, hard candies. The depositor is described in "Sugar Confectionary and Chocolate Manufacture," Leonard Hill Books, Aylesbury, England, 1973, pages 161–190. Depositors are commercially available from Baker Perkins, Ltd., of England. The filled candy is prepared using the depositor at a deposit temperature for the casing of a shell of from about 135° C. to about 155° C. and a deposit temperature for the center of from about 25° C. to about 50° C.

The present invention is illustrated in the following Examples and the prior art is illustrated in the Comparative Examples. In this specification and the appended claims, all parts, percentages and proportions are by weight unless stated otherwise.

In each of the Examples and Comparative Examples and Preparation "L", a Baker-Perkins depositor was used for the depositing process and a microfilm cooker was used to cook the candy base. The experimental procedure for all of the Examples was as follows:

Sucrose and fluidizing agent, if any, are dissolved in water at 100° C. The solution is mixed with corn syrup (43° Be, 42DE) and the resulting product is first pre-heated to 120°–130° C. in a pre-heater coil and then pumped to the top of a heated microfilm cooker. The hot syrup is passed over the rotary blades of the cooker, which spread the syrup in a thin film against the wall of the cooker. The cooker is operated to heat the film of syrup to the desired cooking temperature at atmospheric pressure.

After cooking, the candy base is pumped from the cooker into the depositing hopper of the depositor. The temperature of the candy base is maintained at the desired shell depositing temperature. Pre-heated center material is fed into its hopper and the temperature maintained at the desired center depositing temperature. Liquid center is pumped simultaneously with the candy base shell into molds at a depositing rate of 60 strokes/minute to give 1.0 gram center and 4.0 gram shell. The molds are transferred to a cool room and allowed to set.

In the Examples, liquid center No. 1 or No. 2 was employed. These centers were prepared by cooking the following charges (minus glycerin) to 145°–150°, cooling to 100°–110° C. and then adding the glycerin:

| | Center No. 1 | Center No. 2 |
|---|---|---|
| Glycerin | 36.55 | 31.95 |
| Sucrose | 26.68 | 28.85 |
| Invert Sugar | 3.85 | 4.00 |
| Corn Syrup, 42DE | 29.68 | 31.95 |
| Dextromethorphane base | 0.75 | 0.75 |
| Dextromethorphan.HBr | 0.38 | 0.38 |
| Flavoring and color | 2.11 | 2.11 |

The fully prepared centers had about 5% moisture. Center No. 1 had a viscosity at 50° C. of 7200–7600 cps, and Center No. 2 had a viscosity at 50° C. of 36,900 cps.

EXAMPLE 1

CANDY BASE
 5 lb. mannitol
 55 lb. sucrose
 40 lb. corn syrup
CENTER—Center No. 1
COOKING T—157.6°–158.0° C.
DEPOSIT T (Shell)—156° C.
DEPOSIT T (Center)—40° C.

Liquid center hard candies of good quality were produced. The candies were slightly tacky, but nevertheless satisfactory. The moisture content of the shell was 2.0 to 3.0%.

EXAMPLE II

CANDY BASE
 3 lb. mannitol
 57 lb. sucrose
 40 lb. corn syrup
CENTER—Center No. 1
COOKING T—157.8°–158.9° C.
DEPOSIT T (Shell)—153° C.
DEPOSIT T (Center)—41° C.

There was a slight grain present in the shell at the discharge pipe. This indicates that the ratio of sugar to corn syrup is too high and that 3% mannitol is not sufficient to eliminate all graining during the depositing process. Nevertheless, the candies all had a good deposit of liquid center and were satisfactory.

EXAMPLE III

CANDY BASE
 3 lb. mannitol
 53 lb. sucrose
 44 lb. corn syrup
CENTER—Center No. 1
COOKING T—157°–158° C.
DEPOSIT T (Shell)—150° C.
DEPOSIT T (Center)—42° C.

Liquid center candies of good quantity were obtained, but it was felt that the shell was slightly too viscous for the center under the above conditions. There was no problem with graining at this lower sucrose to glucose ratio. The moisture content of the shell was 2.0 to 3.0%.

This example was then repeated using a high viscosity center, Center No. 2, and excellent results were obtained. The deposit was good, and the candies were satisfactory, but still slightly tacky.

EXAMPLE IV

CANDY BASE
 1.5 lb. mannitol
 1.5 lb. sorbitol
 53 lb. sucrose
 44 lb. corn syrup
CENTER—Center No. 1
COOKING T—157.7°–159° C.
DEPOSIT T (Shell)—156.5° C.
DEPOSIT T (Center)—42.5° C.

The depositing process was carried out successfully and good quality liquid center candies were prepared. The candies were slightly tacky. The moisture content of the shell was 2.0 to 3.0%.

EXAMPLE V

CANDY BASE
 1.0 lb mannitol
 49 lb. sucrose
 50 lb. corn syrup
CENTER—Center No. 1
COOKING T—157°–159° C.
DEPOSIT T (Shell)—150° C.
DEPOSIT T (Center)—41° C.

The candy base was too viscous to deposit properly with the low viscosity center. The center tended to flatten out. The candies were slightly tacky.

EXAMPLE VI

CANDY BASE
 2 lb. mannitol
 48 lb. sucrose
 50 lb. corn syrup
CENTER—Center No. 2
COOKING T—157.1° C.
DEPOSIT T (Shell)—152.5° C.
DEPOSIT T (Center)—42° C.

The depositing process was satisfactory and produced excellent liquid center lozenges. No tackiness was observed. The moisture content of the shell was 2.0 to 3.0%.

As a result of other experiments, it was determined that the tackiness of the candies of Examples I–V was a function of the ambient relative humidity in the cold room. At 56% RH, the problem of tackiness disappeared.

EXAMPLE VII

Samples of candy base (no center fill) were prepared with and without the fluidizing agent at a cooking temperature of 160° C. and stored for six months at room temperature and ambient humidity and at 30° C./80% RH with the following results. In the data which follows, candy base A was 50% sucrose and 50% corn syrup; candy base B was 45% sucrose, 50% corn syrup and 5% mannitol, and candy base C was 50% sucrose, 45% corn syrup and 5% mannitol. The percent crystallization is the percentage of the lozenge cross-sectional area which was crystallized.

| Candy Base | 6 Mo. Room Temp. | | |
|---|---|---|---|
| | % Initial Moisture | % Crystallization | Comments |
| A - (no additive) | 4.2 | 10.0 | Sl tacky, Sl opaque |
| B - (5% mannitol) | 2.8 | 0.0 | Sl tacky, clear |
| C - (5% mannitol) | 2.8 | 0.0 | Vy sl tacky, clear |

| Candy Base | 6 Mo. 30° C./80% R.H. | | |
|---|---|---|---|
| | % Initial Moisture | % Crystallization | Comments |
| A - (no additive) | 4.2 | 80% | Vy tacky, opaque |
| B - (5% mannitol) | 2.8 | 30% | Sl tacky, opaque |
| C - (5% mannitol) | 2.8 | 20% | Not tacky, Sl opaque |

COMPARATIVE EXAMPLE 1

CANDY BASE
 50 lb. sucrose
 50 lb. corn syrup
CENTER—Center No. 1
COOKING T—145° C.
DEPOSIT T (Shell)—145° C.
DEPOSIT T (Center)—40° C.

The deposit of the liquid center was satisfactorily carried out, but the shells burst when the candies were exposed to changing temperatures during transport. The moisture content of the shell was 3.0 to 4.0%.

COMPARATIVE EXAMPLE 2

CANDY BASE
 50 lb. sucrose
 50 lb. corn syrup
COOKING T—155°–175° C.

Despite repeated trials at various cooking temperatures in the range of 155°–175° C., it was not possible to deposit a center material in the candy base shell.

COMPARATIVE EXAMPLE 3

CANDY BASE
 60 lb. sucrose
 40 lb. corn syrup
COOKING T—150° C.

No candy could be produced due to graining of the candy base at the outlet pipe of the microfilm cooker.

PREPARATION "L"

CANDY BASE
 5 lb. lactose
 50 lb. sucrose
 45 lb. corn syrup
 0.3 lb. menthol-eucalyptus flavor
CENTER—Center L-1
COOKING T—160° C.
DEPOSIT T (Shell)—147° C.
DEPOSIT T (Center)—40° C.

Candies with liquid centers were obtained. The center was prepared from:

| CENTER L-1 | |
|---|---|
| | Parts by Weight |
| Glycerin | 60.00 |
| Dextrose, 42DE | 32.85 |
| Dextromethorphan base | 1.10 |
| Keltrol gum | 0.25 |
| Flavoring and color | 5.80 | by cooking all the ingredients except glycerin to 145°–150° C., cooling to 110°–110° C. and then adding glycerin with stirring. The viscosity was 9600 cps at 50° C.

What is claimed is:

1. A candy base which comprises, before cooking, from about 35 to about 60%, by weight, sucrose, from about 55 to about 35%, by weight, corn syrup and from about 1 to about 10% by weight of a fluidizing agent selected from the group consisting of mannitol and a mixture of mannitol and sorbitol having a weight ratio of mannitol to sorbitol of at least about 1:1.

2. The candy base according to claim 1, wherein said corn syrup is regular conversion corn syrup or high maltose corn syrup.

3. The candy base according to claim 1, wherein the amount of sucrose is from about 40 to about 55%, the amount of corn syrup is from about 55 to about 40%, and the amount of said fluidizing agent is from about 2 to about 8%.

4. The candy base according to claim 1, wherein the amount of sucrose is from about 48 to about 53%, the amount of glucose is from about 50 to about 44% and the amount of said fluidizing agent is from about 2 to about 3%.

5. The candy base according to claim 1, wherein said fluidizing agent is a mixture of mannitol and sorbitol having a weight ratio of mannitol to sorbitol of from about 1:1 to about 9:1.

6. The candy base according to claim 1, 2, 3, 4 or 5, wherein said fluidizing agent is mannitol.

7. The candy base according to claim 1, 2, 3, 4 or 5, wherein said fluidizing agent is a mixture of mannitol and sorbitol in a weight ratio of about 1:1.

8. The candy base according to claim 1, 2, 3, 4 or 5 which has been cooked to a moisture content of from about 1.5 to about 3%, by weight.

9. A liquid center, hard candy, which comprises a shell of hard candy comprising the candy base of claim 2 cooked to a moisture content of from about 1.5 to about 3%, by weight, and a liquid center within said shell having a moisture content of from about 5 to about 10% and comprising (a) corn syrup solids, (b) glycerin and (c) sorbitol or a mixture of sucrose and invert sugar.

10. The hard candy according to claim 9, wherein said liquid center has a viscosity of from about 5,000 to about 40,000 cps. when determined at 50° C.

11. The hard candy according to claim 9, wherein said liquid center comprises from about 10 to about 30% sucrose, from about 1 to about 10% invert sugar, from about 30 to about 70% corn syrup solids, from about 20 to about 40% glycerin and from about 5 to about 10% water.

12. The hard candy according to claim 9, wherein said liquid center comprises from about 10 to about 60% sorbitol, from about 10 to about 60% glycerin, from about 30 to about 70% corn syrup solids and from about 5 to about 10% water.

13. The hard candy according to claim 9, 10, 11 or 12, wherein said liquid center contains a therapeutically effective amount of a pharmaceutical compatible with said liquid center.

14. The hard candy according to claim 9, 10, 11 or 12, wherein said liquid center contains a therapeutically effective amount of a pharmaceutical selected from the group consisting of dextromethorphan, phenol, benzocaine and hexylresorcinol.

15. A method of preparing the hard candy according to claim 9, which comprises providing a plurality of candy molds, and sequentially filling each mold by simultaneously pumping into each said mold said liquid center material at a temperature of from about 25° to about 50° C., and said cooked candy base at a temperature of from about 135° C. to about 155° C., and removing said hard candy from said molds after cooling thereof.

16. The method according to claim 15, wherein a high-boil sweets depositor is used for the depositing of the candy into the molds.

* * * * *